United States Patent [19]

Moise

[11] Patent Number: 4,704,121
[45] Date of Patent: Nov. 3, 1987

[54] ANTI-THROMBOGENIC BLOOD PUMP

[75] Inventor: John C. Moise, Carmichael, Calif.

[73] Assignee: Nimbus, Inc., Rancho Cordova, Calif.

[21] Appl. No.: 537,243

[22] Filed: Sep. 28, 1983

[51] Int. Cl.$^4$ .......................... A61F 2/22; F04D 29/04
[52] U.S. Cl. ......................................... 623/3; 415/112
[58] Field of Search .............. 3/1.7; 415/DIG. 4, 111, 415/112, 115, 116; 128/111, 1 R

[56] References Cited

U.S. PATENT DOCUMENTS

| | | | |
|---|---|---|---|
| 3,740,163 | 6/1923 | Schinnerer et al. | 415/111 |
| 4,135,253 | 1/1979 | Reich et al. | 415/DIG. 4 |
| 4,224,008 | 9/1980 | Haentjens | 415/112 |
| 4,236,867 | 12/1980 | Morris | 415/112 |
| 4,239,422 | 12/1980 | Chancey | 415/112 |
| 4,276,002 | 6/1981 | Anderson | 415/112 |

Primary Examiner—Richard J. Apley
Assistant Examiner—David Isabella
Attorney, Agent, or Firm—Weissenberger & Peterson

[57] ABSTRACT

Thrombus formation in an implantable blood pump is prevented by using a close-tolerance purge seal for the impeller shaft or rotor. A blood-compatible fluid is used for the purge fluid (which is preferably also the bearing fluid), and the purge flow into the blood stream presents to the blood stream a benign interface between the rotating and stationary parts of the pump. The rotating and stationary surfaces adjacent the interface are so configured as to present an essentially continuous smooth surface across the interface which can be swept by the blood stream and presents no cavities in which the blood can stagnate. The close clearances of the purge seal allow a sufficient purge flow rate to be maintained with only a minute amount of purge fluid; and in accordance with one aspect of the invention, the purge fluid can be derived from the blood stream by a protein-filtering membrane system so that no external replenishment of the purge fluid supply is necessary.

26 Claims, 7 Drawing Figures

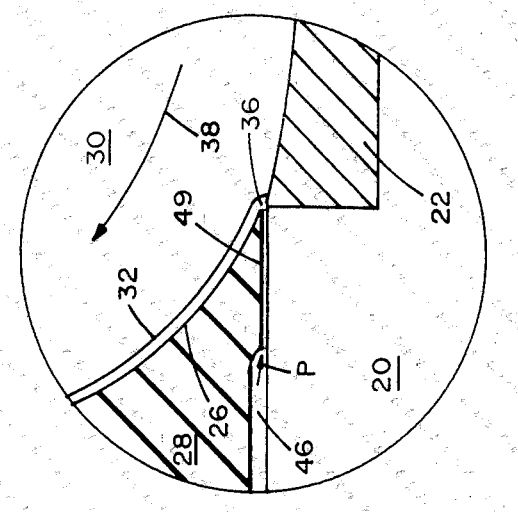
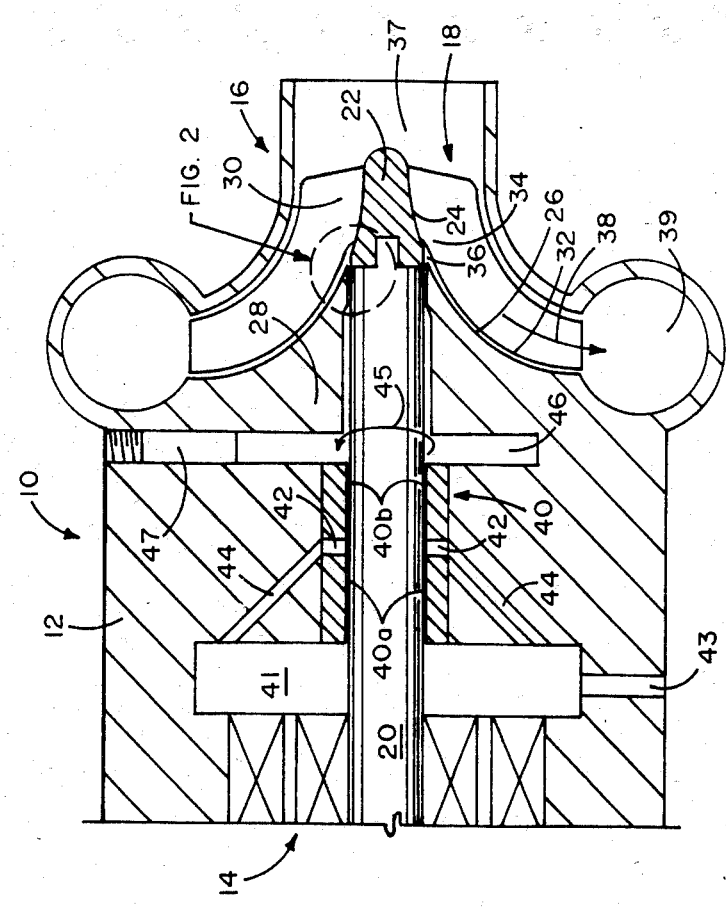

ANTI-THROMBOGENIC BLOOD PUMP

FIELD OF THE INVENTION

This invention relates to continuous delivery blood pumps, and more particularly an implantable blood pump having little or no thrombogenicity and high reliability.

BACKGROUND OF THE INVENTION

Continuous delivery blood pumps used in heart assist applications have inherent size advantages over cyclic delivery blood pumps because they pump all the time and can operate at high speeds. For external temporary assist applications, the cannula size is reduced due to the continuous delivery feature. For implantable pumps, the smaller size of the pump itself eases anatomic placement constraints and allows placements which would otherwise be impossible. Continuous delivery blood pumps do, however, have certain disadvantages. The shear forces created by the relative motion of the impeller and housing may cause hemolysis (i.e. destruction of red cell membranes). Blood elements caught in eddies under the impeller shroud, or stagnating in unswept recesses, are prone to cause accumulations which, among other adverse effects, can produce thrombosis (i.e. the formation of dangerous blood clots). The use of anticoagulants to overcome this problem is not always medically advisable.

Conventional continuous delivery blood pumps have also exhibited serious problems of reliability due to clogging and eventual seizure of the bearings from blood elements entering, and accumulating in, the delicate bearings. Attempts have been made in the prior art (see U.S. Pat. Nos. 4,135,253 to Reich and 3,608,088 to Dorman) to reduce clogging by using hydrodynamic bearings, but any frictional shaft seal contains (or sooner or later develops) small recesses or crevices in which blood elements can become caught to initiate clotting and clogging. Although careful design of the impeller, housing and bearings can reduce its impact, thrombogenicity inherently exists whereever a rubbing interface is present in the blood pump between a rotating part and a stationary part.

SUMMARY OF THE INVENTION

The present invention essentially eliminates the thrombogenicity of the interface between the rotating and stationary parts of the pump by providing a purge seal through which a blood-compatible fluid is introduced into the blood stream at the interface at a flow rate just sufficient to exceed, at all points along the perimeter of the interface, the blood flow rate into the interface caused by diffusion or other mechanisms.

Purge seal techniques are known in technologies relating to the pumping of particulate or abrasive slurries in industry, U.S. Pat. Nos. 4,224,008 to Haentjens, 4,236,867 to Morris, 4,239,422 to Clancey, but the ability of these techniques to prevent thrombosis in blood pumps has not previously been appreciated.

By aligning the rotating part and the stationary part of the interface in such a way as to present an essentially smooth continuous surface to the blood flow, stagnation of blood in the pump is prevented, and the interface appears to the blood flow as a fluid area which is neither hemolytic nor thrombogenic. At the same time, the net purge flow toward the blood stream prevents any blood elements from entering the bearings and causing seizure. When an external purge supply is provided, bacteriostatic fluids such as ethanol may be utilized and anti-thrombogenic agents such as heparin may be added to the fluid to further minimize the tendency to thrombosis in the local region where the purge fluid enters the blood stream.

In accordance with a further aspect of the invention, the purge fluid may be derived from the blood stream by membrane filtration, and the pressure built up in the blood stream by the pump may be used to maintain an adequate purge flow. In this manner, the pump can be operated indefinitely in a purge seal mode without any external source of purge fluid.

It is thus the object of the invention to provide a non-thrombogenic blood pump by using a purge seal to create a benign interface in the blood stream between rotating and stationary parts of the pump.

It is another object of the invention to provide a centrifugal or axial continuous delivery blood pump in which an essentially smooth continuous blood flow path is provided minimizing the possibility of thrombosis.

It is still another object of the invention to provide a blood pump of the type described which requires no external purge fluid source.

BRIEF DESCRIPTION OF THE DRAWINGS

FIG. 1 is a partially schematic vertical section through a centrifugal-flow embodiment of the pump of this invention;

FIG. 2 is an enlarged view of the portion of FIG. 1 lying within the line marked "FIG. 2" in FIG. 1;

DESCRIPTION OF THE PREFERRED EMBODIMENT

Figure 4A:
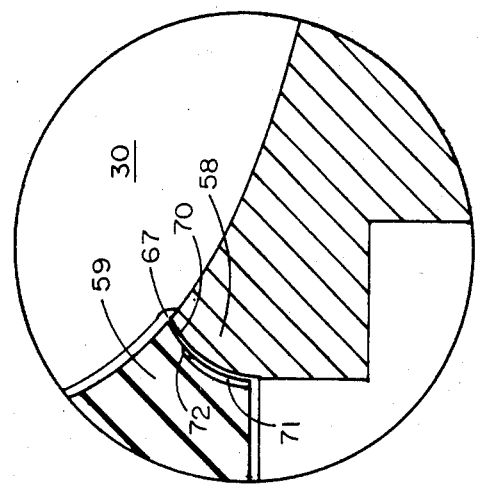
FIG. 4a is an enlarged view, similar to FIG. 2, of an alternative embodiment of the pump of FIG. 1 using spherical bearings.

In FIG. 1, a centrifugal-flow embodiment of the pump of this invention is generally shown at 10. The basic components of the pump are the housing 12, the motor 14 (which is symbolically shown as an electric motor but which may equally well be another type of rotary power device, e.g. driven rotor), and the impeller chamber 16. The impeller 18, a portion of which is shown in more detail in FIG. 2, is driven by the shaft 20 and is shaped to complement the shape of the impeller chamber 16.

Referring to FIG. 2, the impeller 18 has a hub 22 whose surface 24 is curved in such a way as to form a continuation of the curved surface 26 of the interior wall 28 of the impeller chamber 16. The hub 22, which forms the impeller end of shaft 20, carries a plurality of impeller blades 30 of generally conventional design except for the elimination of any shroud on either the front or back of the blades and the fact that their interior edge 32 parallels the curved surface 26 but is spaced therefrom beginning at a point 34 on the hub 22 just short of the interface 36 at which the rotating hub 22 meets the stationary interior wall 28. Blood flows from the central blood inlet 37 to the blood outlet volute 39 in the direction of arrow 38 through the impeller chamber 16. Because of the fact that there is no recess in the hub 22 in which blood can be trapped, the blood stream is continuously swept along the hub surface 24 and the interior wall surface 26.

The bearing 40 is of the hydrodynamic type and rotates on a thin cushion of fluid supplied to it from the cylindrical bearing plenum 42 fed by conduits 44 from the bearing fluid inlet 43. Instead of the split bearing 40a, 40b shown in FIG. 1, a single bearing fed directly from motor cavity 41 may be used. A cylindrical equalizing plenum 46 is provided at the impeller chamber end of the bearing 40 to permit the recirculating end flow of bearing fluid which is characteristic of hydrodynamic bearings. The equalizing plenum 46 may be connected to a low-impedance source of bearing fluid by a conduit 47 if desired.

The impeller chamber wall 28 has a shaft opening 49 (FIG. 2) so dimensioned as to restrict the flow of bearing fluid and to minimize the area of interface 36; however, the axial length of the restricted opening 49 is not sufficient for it to induce significant recirculating flow as a result of bearing action.

The bearing clearances (typically on the order of 2.5 $\mu$m) and the bearing fluid pressures are adjusted in such a manner as to create a purge flow P (FIG. 2) toward the impeller chamber 16 at the interface 36 with a velocity on the order of 0.01 to 0.1 mm/sec. The flow rate should be just sufficient, at all points along the circular interface 36, to overcome any inward flow of blood or blood elements toward the bearing 40. This inward flow is determined by the diffusion rate of the blood elements into the bearing fluid, as well as by other parameters which vary slightly along the perimeter of interface 36. Some of this variation is due to the fact that if the density of the bearing fluid is less than that of the blood, gravity will tend to force more blood toward the bearing on the bottom side of the shaft 20.

As a practical matter, the tolerances and pressures encountered in a typical centrifugal blood pump of this type call for a purge flow rate into the blood stream 38 on the order of 1 cc/day. This minute flow is sufficient to present a fluid barrier to the blood stream at interface 36 to prevent exposure of the blood to the rubbing action of interface 36, which could cause damage to the blood elements and consequent thrombus formation. A uniform blood flow across the interface 36 is maintained by the fact that the interface 36 and the areas adjacent thereto are continuously swept by blood flowing along the hub to the impeller chamber wall 28.

It will be appreciated that the bearing fluid flow along bearings 40 has to be somewhat higher than the purge flow at interface 36, in order to allow the hydrodynamic bearing recirculating flow 45 around the end of bearing 40.

Figure 3:
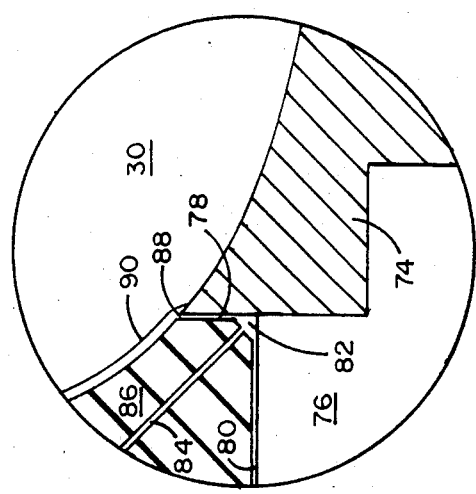
FIG. 3 is an enlarged view, similar to FIG. 2, of an alternative embodiment of the pump of FIG. 1 using a face seal.
Figure 4B:
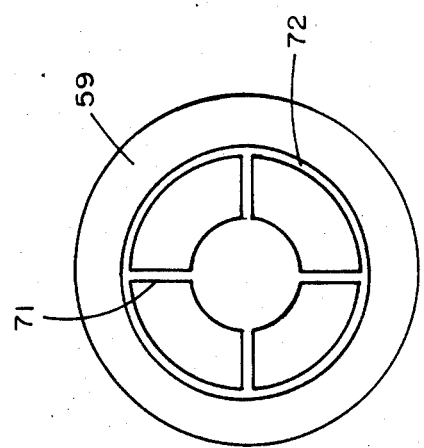
FIG. 4b is an end view of the spherical bearing of FIG. 4a showing the groove pattern therein.
Figure 5:
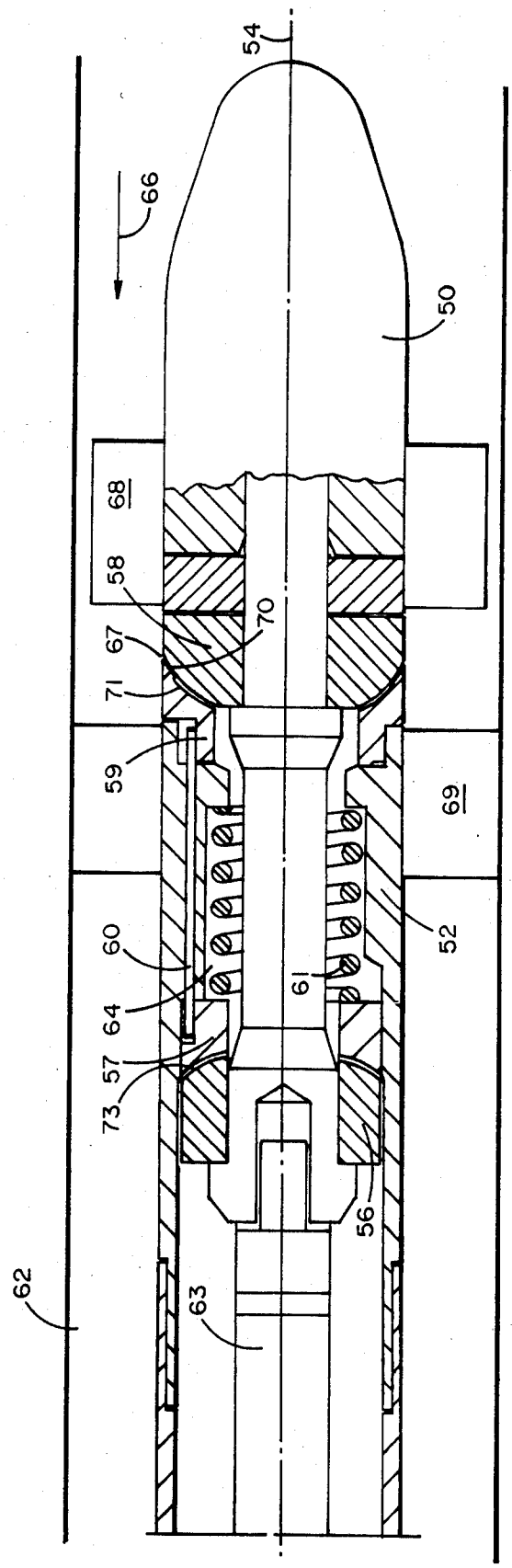
FIG. 5 is a fragmentary axial section through an axial-flow embodiment of the invention using spherical bearings.

FIGS. 3 through 5 depict alternative types of purge seals embodying the invention. Specifically, FIG. 3 illustrates the application of the invention to a face seal. Whereas the seal in the pump of FIGS. 1 and 2 is generally cylindrical, and thus requires an axial purge flow, a face seal (in which the purge flow is radially outward into the blood stream) would also be practical. As shown in FIG. 3, the face seal can optionally also act as a thrust bearing. The face seal arrangement is also frequently useful in axial pumps. FIGS. 4a, 4b, and 5 illustrate a third type of seal usable with both centrifugal and axial blood pumps. This third type is a hybrid seal formed at the end of a spherical bearing which serves as a combination journal and thrust bearing. The principles of this invention are equally applicable to all of these seal configurations.

In the axial-flow blood pump of FIG. 5, a rotor 50 is mounted in a stator 52 for rotation about the axis 54. The rotor 50 is positioned with respect to stator 52 by a pair of spherical bearings 56, 58. The bearings 56, 58 ride against a movable bearing block 57 and a stationary bearing block 59, respectively. Pins 60 prevent rotation of bearing block 57 but allow it to move axially under the bias of spring 61 to maintain close tolerances both in bearing 56 and (by pushing the entire rotor 50 to the left) in bearing 58.

Bearing fluid under pressure is supplied to the pump through cannula 62, which also contains the drive shaft 3 for rotor 50. The bearing fluid flows as a lubricant through bearing 56, and on into the plenum 64 in which the spring 61 is positioned. From there, the bearing fluid flows outwardly through bearing 58, and particularly its seal portion 70, into the blood stream 66 at interface 67. The blood stream 66 is propelled axially through the pump by the interaction of rotor blades 68 and stator blades 69. Although FIG. 5 depicts a single-stage pump, the invention is of course equally applicable to multistage pumps.

As best seen in the enlarged views of FIGS. 4a and 4b, which depict the same spherical bearing 58 but in combination with a centrifugal pump of the type shown in FIG. 1, the spherical purge seal 70 of this invention is formed by the outer portion of the bearing 58 nearest the blood stream In order to minimize the quantity of purge fluid introduced into the blood stream, a very small bearing clearance is essential at the seal 70. Inwardly of the seal 70, however, a greater volume of bearing fluid can be handled for bearing lubrication and hydrodynamic recirculation by providing the bearing block 59 with radial grooves 71 and an annular recirculating channel 72.

Adequate bearing fluid flow through bearing 56 can be assured by extending channels 73 radially throughout the surface of bearing block 57.

Returning now to FIG. 3, the use of a face seal instead of the cylindrical seal of FIG. 2 is illustrated in a centrifugal pump of the general type shown in FIG. 1. In this modification, the inner end of hub 74 is substantially wider than the outer end of shaft 76 to which it is attached. The disc-shaped face seal 78 can, if desired, also serve as a thrust bearing for the shaft 76. Fluid is supplied to the journal bearing 80 and the face seal 78 from an annular plenum 82 fed by a duct 84 in the impeller chamber wall 86. As in the embodiment of FIG. 2, the radial interface 88 is continuously swept by the blood flow from the hub 74 to the impeller blades 90. The radial outflow of bearing fluid from the interface 88 renders the interface 88 benign, and prevents penetration of blood into the thrust bearings 78, in the same manner as discussed above in connection with FIG. 2.

It will be self-evident from the foregoing description that, inasmuch as the bearing fluid in the described embodiments is also used as the purge fluid and is therefore introduced into the blood stream 38, the bearing fluid must be compatible with blood and must also exhibit the necessary hydrodynamic properties required by the bearing 40. Ethanol, physiologic saline solutions, water, and many other substances are suitable for this purpose. Anticoagulants such as heparin or streptokinase may be added to the bearing fluid to further reduce the possibility of thrombus formation at the interface. In addition, the blood pump of this invention may utilize other accepted techniques for minimizing thrombus generation, such as the use of thromboresistant surfaces and avoidance of stagnation areas throughout the pump. However, it should be noted that the use of anticoagulants is not normally necessary with the construction of this invention as it is with most prior art devices, and that the pump of this invention may be of significant benefit in patients who have bleeding problems or in which the use of anticoagulants is contraindicated for some other reason.

Although the invention has been described herein in terms of devices in which the purge fluid is also used to lubricate hydrodynamic bearings, it should be understood that the purge seal may be isolated from the bearings, and the purge fluid used only for seal purposes without departing from the invention. Likewise, rolling contact bearings may be used instead of hydrodynamic bearings if desired.

Figure 6:
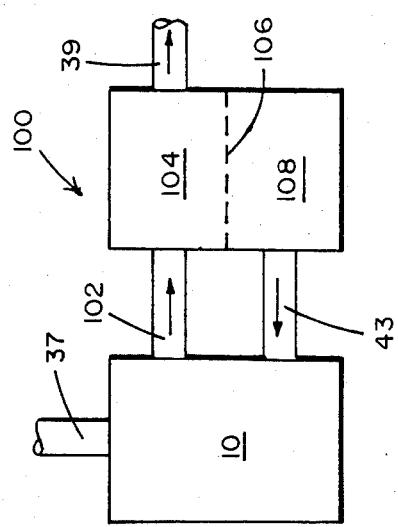
FIG. 6 is a schematic diagram illustrating the derivation of the purge fluid from the blood stream.

Each of the aforementioned purge fluids must be supplied to the pump 10 from some external reservoir or source (not shown) which can be replenished from time to time, albeit infrequently due to the slow purge flow rate. In accordance with a further aspect of the invention, the need for such an external fluid supply can be eliminated entirely by the use of a membrane recirculator 100 as illustrated by the schematic diagram of FIG. 6. In such a device, the blood stream 102 on the outlet side of the pump is exposed to the high-pressure side 104 of a filtration membrane 106. The membrane 106, which passes small molecules such as urea and glucose but excludes proteins, produces a protein-induced osmotic potential of about 22 mmHg. On the low-pressure side of the membrane 106, a bearing fluid in the nature of a proteinfree blood filtrate consisting of water, small molecules (e.g. glucose, urea, and amino acids) and ions capable of penetrating the membrane 106) is recovered. The recovered bearing fluid will have a pressure head, on the low-pressure side 108 of membrane 106, of approximately 78 mmHg. Although losses in the bearing fluid system are likely to bring the pressure down to about 50 mmHg, this is still more than adequate to deliver the required purge flow through the hydraulic path to the purge seal which sees a pressure of approximately 7 mmHg at the discharge from interface 36. The total purge flow available is determined by the area of membrane 106 and can thus be adjusted to suit any particular application.

It will be seen that the invention provides an effective continuous delivery blood pump with minimum tendency to thrombus generation which, if desired, can be implanted in a patient for extended periods of time with minimum risk of blood clots or malfunction.

I claim:

1. An anti-thrombogenic blood pump, comprising:
   (a) a rotor means and stator means cooperating to convey a blood stream through said pump, an interface between said rotor means and stator means being exposed to said blood stream; and
   (b) purge seal means including;
      (i) a source of blood-compatible purge fluid;
      (ii) a continuous passageway formed between said rotor means and stator means between said purge fluid source and said interface, said passageway having a close-clearance, substantially uniform cross section over its entire length from said purge fluid source to said interface; and
      (iii) means for causing said purge fluid to flow continuously and substantially uniformly through said passsageway and into said blood stream stream at said interface;
   (c) whereby said flow substantially pregents the accumulation of blood elements at said interface by preventing entry of blood elements into said interface.

2. The pump of claim 1, in which said rotor means and said stator means are supported for relative rotation by bearing means, and said purge seal means constitute a fluid seal between said blood stream and said bearing means.

3. The pump of claim 2, in which said purge fluid is the bearing fluid used to lubricate said bearing means.

4. The pump of claim 3, in which said bearing means are of the hydrodynamic type, and recirculating means are provided between said bearing means and said purge seal means to prevent the hydrodynamic bearing flow from inducing recirculating effects in said purge seal means.

5. The pump of claim 2, in which the flow of said purge fluid into said blood stream at said interface is just sufficient to prevent blood elements from penetrating said interface.

6. The pump of claim 2, in which said purge seal means is a cylindrical seal.

7. The pump of claim 2, in which said purge seal means is a face seal.

8. The pump of claim 2, in which said purge seal means is a spherical seal.

9. The pump of claim 2, in which said purge fluid consists of protein-free blood filtrate derived from said blood stream.

10. The blood pump of claim 9, in which said filtrate is obtained by providing protein-filtering membrane means having its high-pressure side in operative contact with said blood on the outlet side of said blood pump, and its low-pressure side in operative connectioin with said purge seal means, whereby the protein-free filtrate fluid collected on the low-pressure side of said membrane constitutes the surce of purge fluid for said purge seal means.

11. An anti-thrombogenic centrifugal blood pump, comprising:
   (a) a housing including an impeller chamber;
   (b) driving means disposed in said housing outside said impeller chamber;
   (c) impeller means disposed in said impeller chamber, for centrifugally pumping blood through said impeller chamber;
   (d) shaft means associated with said motor means and impeller means for driving said impeller means;
   (e) said shaft means being rotatably supported in said housing by hydrodynamic journal bearing means operating in a blood-compatible bearing fluid;
   (f) said shaft means and housing forming an interface at said impeller chamber; and
   (g) purge seal means including:
      (i) a source of blood-compatible purge fluid;
      (ii) a continuous passageway formed by said shaft means and said housing between said purge fluid source and said interface, said passageway having a close-clearance, substantially uniform cross section over its entire length from said purge fluid source to said interface; and (iii) means for causing said purge fluid to flow continuously and substantially uniformly through said passageway and into said blood stream at said interface;

(h) whereby said flow substantially prevents the accumulation of blood elements at said interface.

12. The pump of claim 11, in which said impeller means are shroudless.

13. The blood pump of claim 12, in which said impeller means include a hub and a plurality of blades, the surface of said hub and the wall of said impeller chamber forming an essentially continuous smooth surface at the interface between said hub means and said wall.

14. The blood pump of claim 13, in which said blades are arranged to sweep said interface as said impeller means rotate.

15. The blood pump of claim 13, in which said purge fluid flow into said impeller chamber is at a rate just sufficient to overcome the flow of blood or blood elements into said interface at all points along the interface between said shaft means and said housing.

16. The blood pump of claim 11, in which said bearing fluid and said purge fluid are the same fluid.

17. The blood pump of claim 11, further comprising plenum means surrounding said shaft means adjacent said bearing means between said bearing means and said passageway for recirculating said bearing fluid into said bearing means without affecting the flow of said purge fluid into said passageway.

18. The blood pump of claim 17, in which a low-impedance source of bearing fluid is connected to said plenum means.

19. The blood pump of claim 11, in which the clearance of said purge seal means at said interface is on the order of 2.5 $\mu$m.

20. An anti-thrombogenic axial blood pump, comprising:

(a) stator means defining an elongated housing;
(b) rotor means mounted for axial rotation within said housing to convey a blood stream axially of said housing, said rotor means and stator means defining between them an interface in contact with said blood stream;
(c) bearing means for rotatably supporting said rotor means on said stator means; and
(d) purge seal means interposed between said bearing means and said blood stream at said interface for producing an outflow of purge fluid into said blood stream at said interface sufficient to prevent penetration of blood elements into said interface;
(e) said purge seal means including:
 (i) a source of blood-compatible purge fluid;
 (ii) a continuous passageway formed between said rotor means and stator means between said purge fluid source and said interface, said passageway having a substantially uniform, close-clearance cross section over its entire length from said purge fluid source to said interface, and forming a hydrodynamic bearing; and
 (iii) means for causing said purge fluid to flow continuously through said passageway and into said blood stream at said interface;
(f) whereby by said flow substantially prevents the accumulation of blood elements at said interface while providing the bearing fluid for said hydrodynamic bearing.

21. The pump of claim 20, in which the stator and rotor surfaces adjacent said interface form an essentially continuous smooth surface swept by said blood stream.

22. The method of preventing the accumulation of blood elements in a blood pump having a rotor means and stator means cooperating to convey a blood stream through said pump, an interface between said rotor means and stator means being exposed to said blood stream; and purge seal means including;
 (i) a source of blood-compatible purge fluid;
 (ii) a continuous passageway formed between said rotor means and stator means between said purge fluid source and said interface, said passageway having a close-clearance, substantially uniform cross section over its entire length from said purge fluid source to said interface; and
 (iii) means for causing said purge fluid to flow continuously and substantially uniformly through said passageway and into said blood stream at said interface, comprising the steps of (a) so shaping the rotary and stationary parts of said pump that together they form a continuous surface across the interface between them at which said rotating and stationary parts are in contact with the blood being pumped; and
(b) causing a blood-compatible fluid to continuously flow into the pumped blood at all points of said interface;
(c) whereby said flow substantially prevents the accumulation of blood elements at said interface and prevents entry of blood elements into said interface.

23. The method of claim 22, further comprising the step of continually sweeping all of said points during operation of said pump.

24. The method of claim 22, further comprising the step of adjusting the flow rate of said fluid to just slightly exceed the maximum diffusion rate of elements of said blood into said interface along the perimeter of said interface.

25. The method of claim 24, further comprising the step of deriving said fluid by membrane filtration from said blood at a pressure sufficient to produce at least said adjusted flow rate of said fluid.

26. The pump of claim 1, in which the smallest cross section of said passageway is adjacent said interface.

* * * * *

UNITED STATES PATENT AND TRADEMARK OFFICE
CERTIFICATE OF CORRECTION

PATENT NO. : 4,704,121
DATED : 03 November 1987
INVENTOR(S) : J.C. Moise

It is certified that error appears in the above—identified patent and that said Letters Patent is hereby corrected as shown below:

| | |
|---|---|
| Column 1, line 42 | "whereever" should read --wherever--; |
| Column 4, line 20 | "3" should read --63--; |
| Column 4, line 35 | There should be a period after "stream"; |
| Column 6, line 08 | "pregents" should read --prevents--; |
| Column 6, line 46 | "surce" should read --source--; |

Signed and Sealed this

Second Day of August, 1988

Attest:

DONALD J. QUIGG

Attesting Officer

Commissioner of Patents and Trademarks